US009371256B2

(12) United States Patent
Yao et al.

(10) Patent No.: US 9,371,256 B2
(45) Date of Patent: Jun. 21, 2016

(54) THERMAL CRACKING OF IMPURITIES IN TRIGLYCERIDE MIXTURES

(71) Applicants: Jianhua Yao, Bartlesville, OK (US); Edward L. Sughrue, II, Bartlesville, OK (US); Dhananjay B. Ghonasgi, Bartlesville, OK (US); Xiaochun Xu, Bartlesville, OK (US)

(72) Inventors: Jianhua Yao, Bartlesville, OK (US); Edward L. Sughrue, II, Bartlesville, OK (US); Dhananjay B. Ghonasgi, Bartlesville, OK (US); Xiaochun Xu, Bartlesville, OK (US)

(73) Assignee: PHILLIPS 66 COMPANY, Houston, TX (US)

( * ) Notice: Subject to any disclaimer, the term of this patent is extended or adjusted under 35 U.S.C. 154(b) by 16 days.

(21) Appl. No.: 14/230,835

(22) Filed: Mar. 31, 2014

(65) Prior Publication Data

US 2014/0213836 A1   Jul. 31, 2014

Related U.S. Application Data

(63) Continuation-in-part of application No. 12/109,766, filed on Apr. 25, 2008, now Pat. No. 8,017,819, and a continuation-in-part of application No. 13/154,597, filed on Jun. 7, 2011, now abandoned.

(51) Int. Cl.

| | |
|---|---|
| *C07C 1/20* | (2006.01) |
| *C07C 1/22* | (2006.01) |
| *C07C 5/02* | (2006.01) |
| *C10L 1/08* | (2006.01) |
| *C10G 3/00* | (2006.01) |
| *C10G 45/02* | (2006.01) |
| *C10G 69/06* | (2006.01) |
| *C10G 9/00* | (2006.01) |
| *C07C 1/00* | (2006.01) |
| *C07C 1/06* | (2006.01) |
| *C07C 1/213* | (2006.01) |

(52) U.S. Cl.
CPC ... *C07C 1/22* (2013.01); *C07C 5/02* (2013.01); *C10G 3/42* (2013.01); *C10G 3/46* (2013.01); *C10G 3/50* (2013.01); *C10G 9/00* (2013.01); *C10G 45/02* (2013.01); *C10G 69/06* (2013.01); *C10L 1/08* (2013.01); *C10G 2300/107* (2013.01); *C10G 2300/1014* (2013.01); *C10G 2300/1018* (2013.01); *C10G 2300/1037* (2013.01); *C10G 2300/1055* (2013.01); *C10G 2300/1074* (2013.01); *C10G 2300/301* (2013.01); *C10G 2400/04* (2013.01); *Y02E 50/13* (2013.01)

(58) Field of Classification Search
CPC ............ C07C 1/00; C07C 1/06; C07C 1/20; C07C 1/2078; C07C 1/213; C07C 1/22
See application file for complete search history.

(56) References Cited

U.S. PATENT DOCUMENTS

2012/0216450 A1*   8/2012   Dupassieux et al. ............ 44/307

* cited by examiner

*Primary Examiner* — Brian McCaig
(74) *Attorney, Agent, or Firm* — Phillips 66 Company

(57) ABSTRACT

A heated petroleum-derived hydrocarbon is contacted with a triglyceride feed in a thermal cracking zone to decompose and remove impurities prior to hydrotreating the mixture to fuel range hydrocarbon. This process allows the use of a variety of low cost triglyceride feeds while reducing fouling of process equipment and catalyst. The process also reduces the use of chemicals required for conventional degumming of triglyceride feeds.

18 Claims, No Drawings

THERMAL CRACKING OF IMPURITIES IN TRIGLYCERIDE MIXTURES

CROSS-REFERENCE TO RELATED APPLICATIONS

The present invention is a continuation-in-part of U.S. application Ser. No. 12/109,766, now U.S. Pat. No. 8,017,819, filed on Apr. 25, 2008 titled "THERMAL TREATMENT OF TRIGLYCERIDES", and U.S. application Ser. No. 13/154,597 filed on Jun. 7, 2011, abandoned Apr. 10, 2014, titled "THERMAL CRACKING OF IMPURITIES IN TRIGLYCERIDE FEEDSTOCK", both of which are hereby incorporated by reference in their entirety.

STATEMENT REGARDING FEDERALLY SPONSORED RESEARCH OR DEVELOPMENT

None.

FIELD OF THE INVENTION

The present invention relates generally to the thermal cracking of impurities in triglyceride feedstock and in mixtures with petroleum-derived hydrocarbons and the conversion of such mixtures to fuel range hydrocarbons.

BACKGROUND OF THE INVENTION

There is a national interest in the discovery of alternative sources of fuels and chemicals, other than from petroleum resources. As the public discussion concerning the availability of petroleum resources and the need for alternative sources continues, government mandates will require transportation fuels to include, at least in part, hydrocarbons derived from sources besides petroleum. As such, there is a need to develop alternative sources for hydrocarbons useful for producing fuels and chemicals.

One possible alternative source of hydrocarbons for producing fuels and chemicals is the natural carbon found in plants and animals, such as for example, oils and fats. These so-called "natural" carbon resources (or renewable hydrocarbons) are widely available, and remain a target alternative source for the production of hydrocarbons. For example, it is known that oils and fats, such as those contained in vegetable oil, can be processed and used as fuel. Biodiesel is one such product and may be produced by subjecting a base biomass-derived oil to a transesterification process using methanol in order to convert the oil to desired methyl esters. After processing, the products produced have very similar combustion properties as compared to petroleum-derived hydrocarbons. However, the use of biodiesel as an alternative fuel has not yet been proven to be cost effective. In addition, biodiesel often exhibits poor cold flow properties, which limits its use in pure form in cold climates.

Unmodified vegetable oils and fats have also been used as additives in diesel fuel to improve the qualities of the diesel fuel, such as for example, the lubricity. However, problems such as injector coking and the degradation of combustion chamber conditions have been associated with these unmodified additives. Since cetane ($C_{16}H_{34}$), heptadecane ($C_{17}H_{36}$) and octadecane ($C_{18}H_{38}$) by definition have very good ignition properties (expressed as cetane rating), it is often desired to add paraffinic hydrocarbons in the $C_{16}$-$C_{18}$ range, provided that other properties of the additive (such as for example, viscosity, pour point, cloud point, etc.) are congruent with those of the diesel fuel. Processes for converting biomass-derived oils into hydrocarbons have been achieved, such as, for example, contacting a diesel/vegetable oil mixture with a hydrotreating catalyst. However, triglyceride feeds often contain significant amounts of impurities such as such as phospho-lipids, proteins, gums, and other metal containing compounds (such as alkali metals, alkaline earth metals). These impurities can cause catalyst deactivation and plugging of the hydrotreating reactor catalyst bed as well as fouling of heat exchangers and other process equipment.

As such, development of a new and simple process for removing impurities such as phospho-lipids, proteins, gums, metal containing compounds (such as alkali metals, alkaline earth metals) from such oils would be a significant contribution to the art.

BRIEF SUMMARY

In certain embodiments, the inventive process comprises the steps of: a) obtaining a hydrocarbon feed derived from petroleum that comprises compounds having a boiling point from about 25° C. to about 760° C.; b) heating the hydrocarbon feed to a temperature ranging from about 100° C. to about 540° C. to produce a heated hydrocarbon feed; c) conveying the heated hydrocarbon feed to a thermal cracking zone; d) contacting a triglyceride feed with the heated hydrocarbon feed in the thermal cracking zone at a temperature ranging from about 100° C. to about 540° C. to form a thermally-treated feed, where the contacting results in the thermal cracking of at least one contaminant derived from the triglyceride feed to form a decomposed contaminant, where the contaminant may be phospholipids, proteins, gums, a metal containing compound or any combination of these contaminants, and where the metal containing compound may be alkali metals, alkaline earth metals, or any combination of these; e) conveying the thermally treated feed to a hydrotreating zone; f) hydrotreating the thermally treated feed with a hydrotreating catalyst in the hydrotreating zone at a temperature in the range of from about 260° C. to about 430° C. and a pressure ranging from 0 psig to about 2000 psig to produce a product containing diesel boiling range hydrocarbons.

In certain embodiments, the sole source of heat for the thermal cracking zone is the heated hydrocarbon feed. Preferably, the triglyceride feed is maintained at a temperature that does not thermally crack the contaminant prior to contacting the heated hydrocarbon feed in the thermal cracking zone. The thermal cracking of the contaminant may produce a decomposed contaminant that is more easily removed from the thermally treated feed. Removal of the decomposed contaminant may be achieved by precipitation followed by sedimentation and collection, filtration, absorption, adsorption, or any combination of these. Collection of sediment is optionally facilitated by the design of the thermal cracking zone or the retention zone.

The inventive process allows cleaning the feedstock in situ and reduces or eliminates the need for conventional de-gumming of the biomass prior to use. This enables the use of a variety of low cost biomass feedstock in the process and reduces fouling of reactors, heat exchangers and hydrotreating catalysts.

Other objects, advantages and embodiments of the invention will be apparent from the following detailed description of the invention and the appended claims.

BRIEF DESCRIPTION OF THE DRAWINGS

None

DETAILED DESCRIPTION

Turning now to the detailed description of the embodiments of the present invention. It should be understood that the inventive features and concepts may be manifested in other arrangements and that the scope of the invention is not limited to the embodiments described or illustrated. The scope of the invention is intended only to be limited by the scope of the claims that follow.

Triglycerides, fatty acids of triglycerides, or mixtures thereof, may be converted to form a hydrocarbon mixture useful for liquid fuels and chemicals. The term, "triglyceride," is used generally to refer to any naturally occurring ester of a fatty acid and/or glycerol having the general formula $CH_2(OCOR_1)CH(OCOR_2)CH_2(OCOR_3)$, where $R_1$, $R_2$, and $R_3$ are the same or different, and may vary in chain length. Vegetable oils, such as for example, canola and soybean oils contain triglycerides with three fatty acid chains. Useful triglyceride feeds in the present invention include, but are not limited to, triglycerides that may be converted to hydrocarbons when contacted under suitable reaction conditions. Examples of triglycerides useful in the present invention include, but are not limited to, vegetable oils including soybean and corn oil, peanut oil, sunflower seed oil, coconut oil, babassu oil, grape seed oil, poppy seed oil, almond oil, hazelnut oil, walnut oil, olive oil, avocado oil, sesame, oil, tall oil, cottonseed oil, palm oil, ricebran oil, canola oil, cocoa butter, shea butter, butyrospermum, wheat germ oil, illipse butter, meadowfoam, seed oil, rapeseed oil, borange seed oil, linseed oil, castor oil, vernoia oil, tung oil, jojoba oil, ongokea oil, algae oil, jatrothea oil, yellow grease (for example, as those derived from used cooking oils), and animal fats, such as poultry grease, beef fat (tallow), and milk fat, and the like and mixtures and any combination thereof.

In the processes described herein, the triglyceride feed is co-processed in combination with a petroleum-derived hydrocarbon feed to produce fuel-range hydrocarbons, and preferably, diesel boiling range hydrocarbons. The petroleum-derived hydrocarbon feed is typically composed of compounds that boil at a temperature of from about 25° C. to about 760° C. One examples of a petroleum-derived hydrocarbon feed suitable for the process includes a middle distillate fuel. Middle distillate fuels generally contain hydrocarbons that boil in the range from about 150° C. to about 400° C. Typical middle distillates may include, for example, jet fuel, kerosene, diesel fuel, light cycle oil, atmospheric gas oil, and vacuum gas oil. If a middle distillate feed is employed in a given embodiment, the feed generally may contain a mixture of hydrocarbons having a boiling range (ASTM D86) of from about 150° C. to about 400° C., with a mid-boiling point (ASTM D86) of greater than about 175° C. An exemplary middle distillate feed employed in one embodiment is diesel fuel. In addition to middle distillate fuels, other suitable hydrocarbons include, but are not limited to, gasoline, naphtha, and atmospheric tower bottom.

Generally, the petroleum-derived hydrocarbon can contain a quantity of sulfur that is generally greater than about 20 parts per million by weight (ppmw) sulfur. In one embodiment of the present invention, sulfur is present in an amount in the range of from about 100 ppmw to about 50,000 ppmw sulfur. In another embodiment of the present invention, sulfur is present in the range of from about 150 ppmw to 4,000 ppmw. As used herein, the term "sulfur" denotes elemental sulfur, and also any sulfur compounds normally present in a hydrocarbon stream, such as diesel fuel. Examples of sulfur compounds which may be contained in the hydrocarbon through in the present invention include, but are not limited to, hydrogen sulfide, carbonyl sulfide (COS), carbon disulfide (CS) mercaptans (RSH), organic sulfides (R—S—R), organic disulfides (R—S—S—R), thiophene, substituted thiophenes, organic trisulfides, organic tetrasulfides, benzothiophene, alkyl thiophenes, dibenzothiophene, alkyl benzothiophenes, alkyl dibenzothiophenes, and the like, and mixtures thereof as well as heavier molecular weights of the same, wherein each R can be an alkyl, cycloalkyl, or aryl group containing 1 to about 10 carbon atoms.

Generally, the triglyceride feed contains a certain amount of impurities, or contaminants that can cause catalyst deactivation and plugging of the hydrotreating catalyst as well as fouling of heat exchangers, reactors, and other process equipment. Examples of such contaminants typically include phospho-lipids, proteins, gums, metal containing compounds (such as alkali metals, alkaline earth metals), and any combination thereof. The quantities of these contaminants are generally in the range of from about 0 ppmw to about 10,000 ppmw.

The present processes quickly remove such contaminants by thermal cracking of the contaminants while preventing thermal cracking of most, or all, triglycerides in the feed. In certain embodiments, contacting of the triglyceride feed with the heated hydrocarbon feed in the thermal cracking reactor results in the thermal cracking of less than 5 weight percent, 2 weight percent, or even less than 1 weight percent of the triglycerides in the triglyceride feed. In certain embodiments, contacting the triglyceride feed with the heated hydrocarbon feed does not result in the thermal cracking of triglycerides in the triglyceride feed.

The petroleum-derived feed is heated to a temperature ranging from about 100° C. to about 540° C. to produce a heated hydrocarbon feed. The triglyceride feed is not mixed with the petroleum-derived feed prior to this heating step in order to avoid fouling of heat exchangers and process equipment upstream from the thermal cracking zone. Heating of the petroleum derived feed may be accomplished by any known mechanism, such as via a conventional heat exchanger. The heated hydrocarbon feed is then conveyed to a thermal cracking zone where it is contacted with the triglyceride feed at a temperature ranging from about 100° C. to about 540° C. to form a thermally-treated feed. Optionally, the temperature in the thermal cracking zone is in the range of from about 120° C. to about 430° C., optionally from about 200° C. to about 400° C., optionally from about 225° C. to about 375° C. The liquid hourly space velocity (LHSV) in the thermal cracking zone typically ranges from about 0.2 $hr^{-1}$ about 5 $hr^{-1}$.

The contacting of the triglyceride feed with the petroleum-derived feed in the thermal cracking zone results in the thermal cracking of at least one contaminant derived from the triglyceride feed to form a decomposed contaminant, where the contaminant may be phospholipids, proteins, gums, a metal containing compound or any combination of these contaminants, and where the metal containing compound may be alkali metals, alkaline earth metals, or any combination of these.

The thermally-treated feed is then conveyed to a hydrotreating zone where it contacts a hydrotreating catalyst at a temperature in the range of from about 260° C. to about 430° C. and a pressure ranging from 0 psig to about 2000 psig to produce a product containing diesel boiling range hydrocarbons.

In certain embodiments, the sole source of heat for the thermal cracking zone is the heated hydrocarbon feed. Preferably, the triglyceride feed is maintained at a temperature that does not permit thermal cracking of the contaminant prior to contacting the heated hydrocarbon feed in the thermal cracking zone.

A benefit of the present processes is that decomposed contaminants are often more easily removed from the thermally treated feed, thereby allowing a greater percentage of contaminants to be removed from the feeds and preventing downstream fouling of process equipment and catalyst deactivation.

In certain instances, the decomposed contaminant may precipitate for a variety of reasons, including, for example, polymerization of the contaminant following thermal cracking. In certain embodiments, retention of the decomposed contaminant is achieved by precipitation followed by sedimentation and collection, filtration, absorption, adsorption, or any combination of these. It should be noted that in certain embodiments, a lesser amount of one or more contaminants not decomposed in the thermal cracking zone may still be retained by these mechanisms.

In certain embodiments, thermal cracking of the contaminant facilitates retention of the decomposed contaminant in a retention zone, which may help prevent contact between the decomposed contaminant and the hydrotreating catalyst. This retention zone may overlap or coincide with at least a portion of the thermal cracking zone, or alternatively may be located downstream, between the thermal cracking zone and the hydrotreating zone.

Collection or retention of sediment may be facilitated by the design of the retention zone. The retention zone may comprise, for example, a depression, receptacle, or container into which precipitated decomposed contaminant can sediment and be retained. In certain embodiments, sediment comprising decomposed contaminant can be removed either continuously or periodically from the retention zone. Such design may optionally work in conjunction with any of the other strategies described above to facilitate retention of the decomposed contaminant.

As stated, the triglyceride feed contacts the petroleum-derived hydrocarbon feed in the thermal cracking zone to form a thermally treated feed. Generally, the triglyceride feed may comprise in the range of from about 0.1 weight percent to about 99.9 weight percent of the thermally treated feed. Alternatively, the triglyceride feed may be present in an amount in the range of from about 2 weight percent to about 80 weight percent, from about 10 weight percent to about 60 weight percent, or from about 50 weight percent to about 99.9 weight percent of the thermally treated feed.

In certain embodiments, contacting of the triglyceride feed with the heated hydrocarbon feed results in the thermal cracking of less than 5%, 2%, or even less than 1% (by weight) of the triglycerides in the triglyceride feed. Preferably, contacting the triglyceride feed with the heated hydrocarbon feed does not result in the thermal cracking of triglycerides in the triglyceride feed.

A typical degumming process for triglycerides involves contacting the triglycerides with a water wash. In the present inventive processes, subjecting the triglyceride feed to a degumming process is optional, and one potential benefit of the inventive processes is the ability to omit this degumming of the triglyceride feed without adversely affecting the hydrotreating catalyst or process equipment.

In one embodiment of the present invention, the triglyceride feedstock or its mixture with petroleum derived feed hydrocarbon may be contacted with an inert co-feed gas in the thermal cracking zone, such as nitrogen, helium, carbon monoxide, carbon dioxide or mixtures of any of these gases. Preferably, the co-feed gas in the thermal cracking zone is not a reactive gas such as, for example, hydrogen. Not wishing to be bound by theory, it is thought that the presence of hydrogen during thermal cracking may prevent efficient or complete decomposition of contaminants in the thermal cracking zone, thereby decreasing the effectiveness of the inventive processes disclosed herein.

Thermal cracking generally refers to heating a material in the absence of oxygen or air. Thermal cracking generally results in decomposition of thermally unstable components of the feedstock, such as phospho-lipids, proteins, gums, and other metal containing compounds. The thermally unstable material decomposes and is removed from the feed while optimally leaving cleaner triglycerides unaffected and suitable for downstream hydrotreating to fuel range hydrocarbons.

Generally, a thermally treated feed from any one of the previous embodiments can be contacted with a catalyst composition under conditions sufficient to produce a reaction product comprising fuel range hydrocarbons, preferably diesel boiling range hydrocarbons. Useful catalyst compositions in the present invention include catalysts effective in the conversion of triglycerides to hydrocarbons when contacted under suitable reaction conditions. Examples of suitable catalysts include hydrotreating catalysts. The term "hydrotreating" as used herein, generally describes a catalyst that is capable of utilizing hydrogen to accomplish saturation of unsaturated materials, such as aromatic compounds. Examples of hydrotreating catalysts useful in the present invention include, but are not limited to, materials containing compounds selected from Group VI and Group VIII metals, and their oxides and sulfides. Examples of hydrotreating catalysts include but are not limited to alumina supported cobalt-molybdenum, nickel sulfide, nickel-tungsten, cobalt-tungsten and nickel-molybdenum.

The metal of the catalyst useful in the present invention is usually distributed over the surface of a support in a manner than maximizes the surface area of the metal. Examples of suitable support materials for the hydrogenation catalysts include, but are not limited to, silica, silica-alumina, aluminum oxide ($Al_2O_3$), silica-magnesia, silica-titania and acidic zeolites of natural or synthetic origin. The metal catalyst may be prepared by any method known in the art, including combining the metal with the support using conventional means including but not limited to impregnation, ion exchange and vapor deposition. In an embodiment of the present invention, the catalyst contains molybdenum and cobalt supported on alumina or molybdenum and nickel supported on alumina.

This process in accordance with an embodiment of the present invention can be carried out in any suitable reaction zone that enables intimate contact of the thermally cracked feed and control of the operating conditions under a set of reaction conditions that include total pressure, temperature, liquid hourly space velocity, and hydrogen flow rate. The catalyst can be added first to the reactants and thereafter, fed with hydrogen. In the present invention, either fixed bed reactors or fluidized bed reactors can be used. As used herein, the term "fluidized bed reactor" denotes a reactor wherein a fluid feed can be contacted with solid particles in a manner such that the solid particles are at least partly suspended within the reaction zone by the flow of the fluid feed through the reaction zone and the solid particles are substantially free to move about within the reaction zone as driven by the flow of the fluid feed through the reaction zone. As used herein, the term "fluid" denotes gas, liquid, vapor and combinations thereof.

Generally, the reaction conditions at which the hydrotreating zone is maintained include a temperature in the range of from about 260° C. to about 430° C. Preferably, the temperature is in the range of from about 310° C. to about 370° C.

In accordance with the present invention, regardless of whether a fixed or fluidized bed is utilized in the hydrotreating zone, the pressure is generally maintained in the range of from about 100 pounds per square inch gauge (psig) to about 2000 psig. Generally, when the hydrotreating zone comprises a fixed bed reactor, the pressure is in the range of from about 100 psig to about 1500 psig. When the hydrotreating zone comprises a fixed bed reactor, the pressure can also be about 600 psig. When the hydrotreating zone comprises a fluidized bed reactor, the pressure is generally in the range of from about 400 psig to about 750 psig, and can also be about 500 psig.

The following examples are presented to further illustrate the processes described herein, and are not to be construed as unduly limiting the scope of the invention.

Example 1

Undegummed vegetable oil was diluted in an undesulfurized diesel fuel to provide a mixture containing 10% vegetable oil. The mixture was mixed with either hydrogen or nitrogen and was fed into a heated ¼-inch diameter tube. The feed was exposed to a temperature of 348° C. for about 20 seconds. This run was done with hydrogen as a co-feed, and another with nitrogen as a co-feed. The feed and product metal concentrations are shown in Table I, below.

TABLE I

| Thermal Cracking of Vegetable Oil | | | |
|---|---|---|---|
| Description | Feed | Product 1 | Product 2 |
| Treatment Temperature, ° C. | | 348 | 348 |
| Treatment Pressure, psig | | 200 | 200 |
| Co-feed Gas | | $H_2$ | $N_2$ |
| ICP metal, ppm | | | |
| Potassium | 18.9 | 1.6 | 1.6 |
| Calcium | 7.6 | 1.0 | 1.0 |
| Magnesium | 7.4 | 0.9 | 1.1 |
| Phosphorus | 47.6 | 10.5 | 13.6 |
| Total | 81.5 | 14.1 | 17.3 |

The result of example 1 demonstrated the total metals and phosphorus removal of about 80%.

Example 2

A mixture of soybean oil and diesel was fed into a heated tube operated at a temperature of about 330° C. and a pressure of 700 psig (there was no co-feed gas present). The mixture was then passed through a filter and sent to a hydrotreating reactor containing a hydrotreating catalyst. Table 2 below shows that the hydrotreating reactor experienced no pressure drop, unlike when the same mixture is fed through a hydrotreating reactor without the pre-treatment.

TABLE 2

| Reactor Configuration | Hydrotreating Reactor Only | Heated Tube/Filter/Hydrotreating Reactor |
|---|---|---|
| Time On-Stream, hrs | 50 | 100 |
| Reactor Pressure Drop, psig | 100 | None |

In closing, it should be noted that the discussion of any reference is not an admission that it is prior art to the present invention, especially any reference that may have a publication date after the priority date of this application. At the same time, each and every claim below is hereby incorporated into this detailed description or specification as an additional embodiment of the present invention.

Although the systems and processes described herein have been described in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims while the description, abstract and drawings are not to be used to limit the scope of the invention. The invention is specifically intended to be as broad as the claims below and their equivalents.

The invention claimed is:
1. A process comprising:
a) obtaining a petroleum-derived hydrocarbon feed that comprises hydrocarbon compounds having a boiling point from about 25° C. to about 760° C.;
b) heating the petroleum-derived hydrocarbon feed to a temperature ranging from about 100° C. to about 540° C. to produce a heated hydrocarbon feed;
c) conveying the heated hydrocarbon feed to a thermal cracking zone;
d) contacting a triglyceride feed with the heated hydrocarbon feed in the thermal cracking zone at a temperature ranging from about 100° C. to about 540° C. to form a thermally treated feed, wherein the contacting results in the thermal cracking of at least one contaminant derived from the triglyceride feed to form a decomposed contaminant, wherein the contaminant is selected from phospholipids, proteins, gums, metal containing compound and any combination thereof, wherein the metal containing compound is selected from alkali metals, alkaline earth metals, and any combination thereof, wherein the thermal cracking facilitates retention of the decomposed contaminant and prevents contact between the decomposed contaminant and the hydrotreating catalyst;
e) conveying the thermally treated feed to a hydrotreating zone;
f) hydrotreating the thermally treated feed with a hydrotreating catalyst in the hydrotreating zone at a temperature in the range of from about 260° C. to about 430° C. and a pressure ranging from 0 psig to about 2000 psig to produce a product containing diesel boiling range hydrocarbons, wherein hydrogen is added only downstream from the retention of the decomposed contaminant.
2. The process of claim 1, wherein the sole source of heat for the thermal cracking zone is the heated hydrocarbon feed.

3. The process of claim 1, wherein the triglyceride feed is maintained at a temperature that does not permit thermal cracking of the contaminant prior to the triglyceride feed contacting the heated hydrocarbon feed in the thermal cracking zone.

4. The process of claim 1, wherein retention of the decomposed contaminant is achieved by precipitation followed by sedimentation and collection, filtration, absorption, adsorption, or any combination thereof.

5. The process of claim 4, wherein sedimentation and collection is facilitated by the design of the thermal cracking zone.

6. The process of claim 1, wherein the contacting of the triglyceride feed with the heated hydrocarbon feed results in the thermal cracking of less than 5 percent (by weight) of the triglycerides in the triglyceride feed.

7. The process of claim 1, wherein the contacting of the triglyceride feed with the heated hydrocarbon feed results in the thermal cracking of less than 2 percent (by weight) of the triglycerides in the triglyceride feed.

8. The process of claim 1, wherein the contacting of the triglyceride feed with the heated hydrocarbon feed results in the thermal cracking of less than 1 percent (by weight) of the triglycerides in the triglyceride feed.

9. The process of claim 1, wherein the contacting of the triglyceride feed with the heated hydrocarbon feed does not result in the thermal cracking of triglycerides in the triglyceride feed.

10. The process of claim 1, wherein the temperature in the thermal cracking zone is in the range of from about 120° C. to about 430° C.

11. The process of claim 1, wherein the temperature in the thermal cracking zone is in the range of from about 200° C. to about 400° C.

12. The process of claim 1, wherein the temperature in the thermal cracking zone is in the range of from about 225° C. to about 375° C.

13. The process of claim 1, wherein the pressure in the thermal cracking zone is in the range of from about 0 psig to about 2000 psig.

14. The process of claim 1, wherein the triglyceride feed is not subjected to a degumming process prior to contacting the heated hydrocarbon feed in the thermal cracking zone.

15. The process of claim 1, wherein the thermal cracking is performed in the presence of an inert co-feed gas selected from, nitrogen, helium, carbon monoxide, carbon dioxide and any combination thereof.

16. The process of claim 1, wherein the triglyceride feed comprises from about 2 percent (by weight) to about 80 percent (by weight) of the thermally treated feed.

17. The process of claim 1, wherein the triglyceride feed comprises from about 10 percent (by weight) to about 60 percent (by weight) of the thermally treated feed.

18. The process of claim 1, wherein the hydrocarbon feed is selected from gasoline, naphtha, jet fuel, kerosene, diesel fuel, light cycle oil, vacuum gas oil, atmospheric gas oil, atmospheric tower bottom, and any combination thereof.

* * * * *